United States Patent [19]

Grundei et al.

[11] 4,064,568
[45] Dec. 27, 1977

[54] KNEE-JOINT ENDOPROSTHESES

[75] Inventors: Hans Grundei; Wolfram Thomas, both of Lubeck, Germany

[73] Assignee: Sanitatshaus Schuutt & Grundei, Luebeck, Germany

[21] Appl. No.: 739,819

[22] Filed: Nov. 8, 1976

[30] Foreign Application Priority Data

Nov. 6, 1975   Germany .............................. 2549819

[51] Int. Cl.² ................................................. A61F 1/24
[52] U.S. Cl. ..................................... 3/1.911; 128/92 C
[58] Field of Search .......................... 3/1.911, 1.91, 1.9, 3/22; 128/92 C

[56]   References Cited

U.S. PATENT DOCUMENTS

| 3,805,302 | 4/1974  | Mathys ........................ 3/1.91 |
| 3,837,009 | 9/1974  | Walker ....................... 3/1.911 |
| 3,840,905 | 10/1974 | Deane ........................ 3/1.911 |
| 3,869,729 | 3/1975  | Attenborough ............. 3/1.91 |

FOREIGN PATENT DOCUMENTS

| 2,122,390 | 1/1973  | Germany ..................... 3/1.911 |
| 2,152,408 | 4/1973  | Germany ..................... 3/22 |
| 2,244,064 | 3/1974  | Germany ..................... 3/1.911 |
| 2,306,552 | 8/1974  | Germany ..................... 3/1.91 |
| 1,333,412 | 10/1973 | United Kingdom ........... 3/1.911 |

Primary Examiner—Ronald L. Frinks
Attorney, Agent, or Firm—Kinzer, Plyer, Dorn & McEachran

[57]  ABSTRACT

A knee-joint endoprosthesis comprising an upper and lower shank for attachment to the femur and tibia and provided with two pads which are yoked together across a central ridge. In such an endoprosthesis, the invention provides the improvement which consists in that a saddle-shaped ridge is provided with a fixed guiding cross-shaft which forms a free spigot on either side of said ridge and which lies off and to the rear of the center axis of said lower shank when the joint is in the extended position, in that two curved, hollowed-out bearing faces, and said supporting pads, which conform to said bearing faces in the extended position, diminish in width from front to rear as a result of said ridge becoming wider in the rearwards direction, in that said spigots engage with clearance in guide grooves in said supporting pads which extend approximately parallel to the lower faces of said pads and which open upwards at their rear ends, and in that the extension of the two sections of the joint is restricted by an abutment.

6 Claims, 8 Drawing Figures

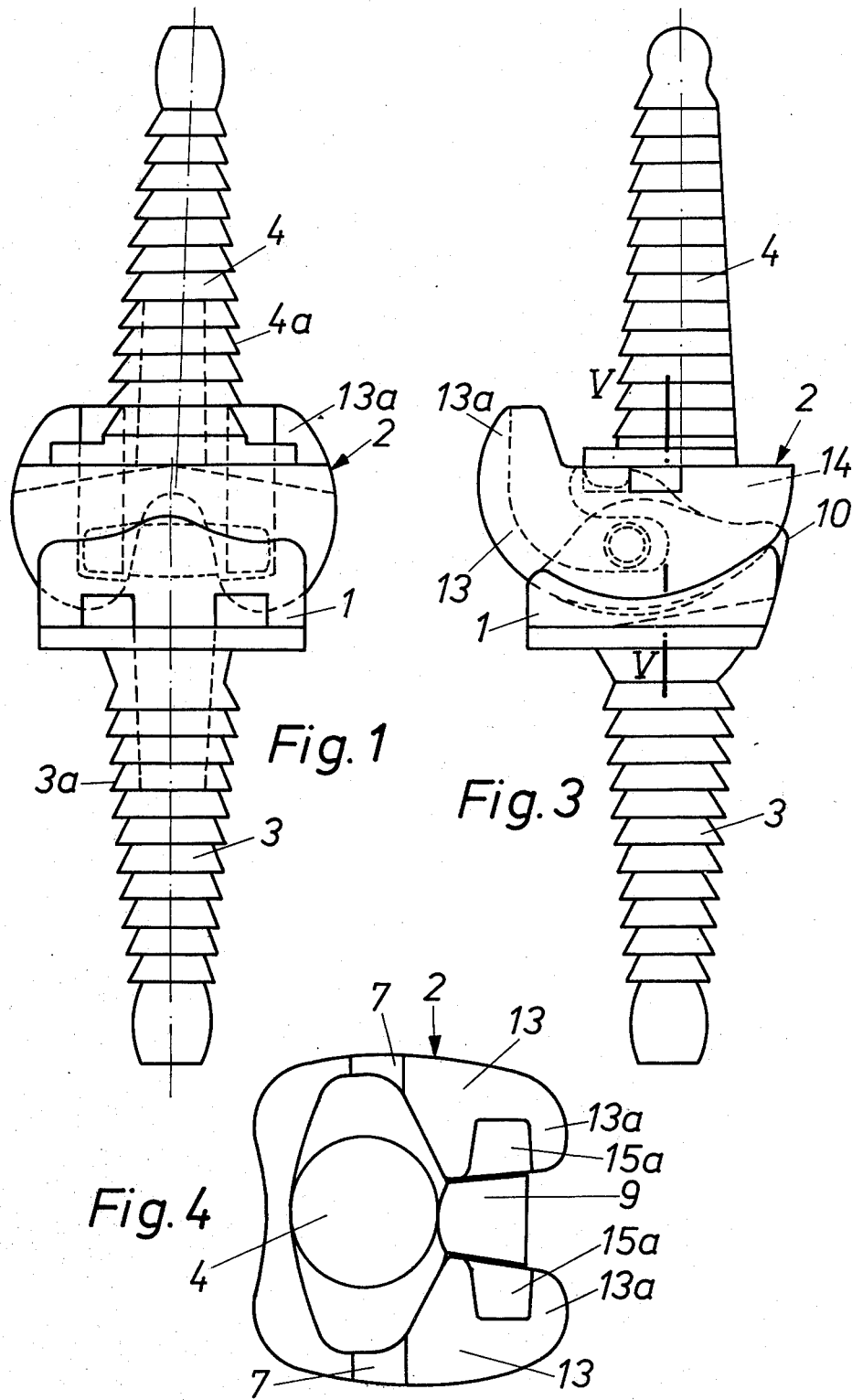

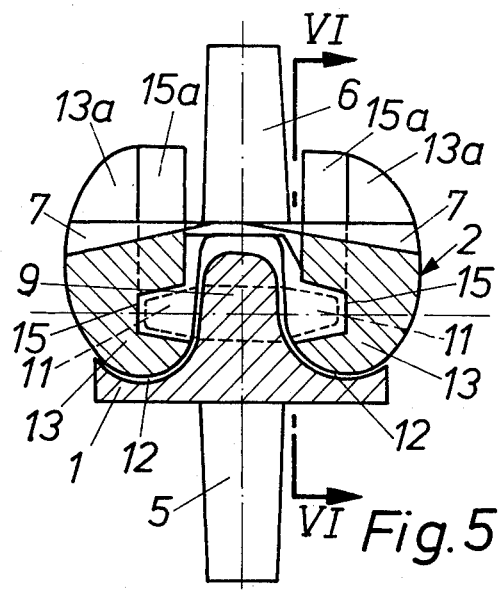
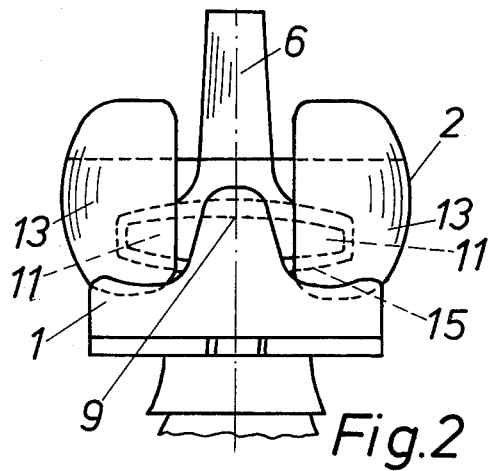
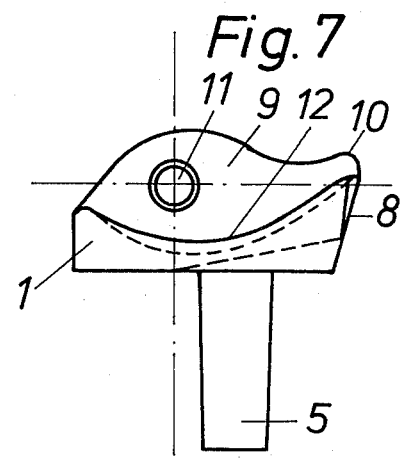
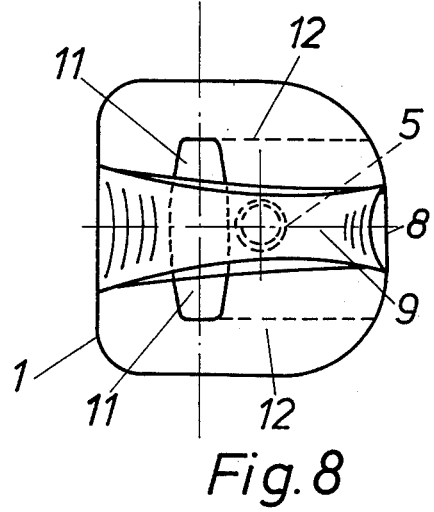
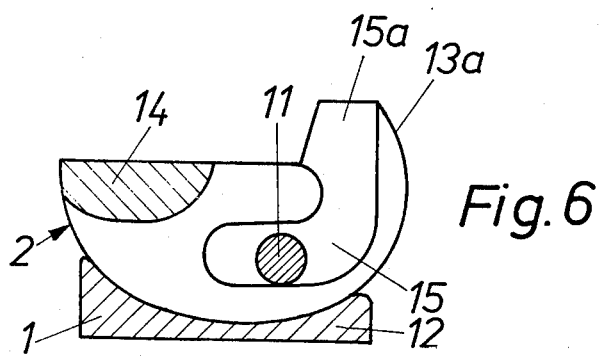

KNEE-JOINT ENDOPROSTHESES

BACKGROUND OF THE INVENTION

The present invention relates to knee-joint endoprostheses of the kind consisting of a lower, tibia section to be anchored in the shin-bone by a shank, which section has, on either side of a central ridge which extends from front to rear, a bearing face which rises in a curve towards the front and which is hollowed out in cross-section, and of a femur section which is to be anchored in the thigh bone by a shank and which is provided with two pads which are yoked together across the ridge and are supported on the bearing faces.

Known knee-joint endoprostheses of the kind described above have to be screwed together when the operation is performed to fit them and in them, when the knee is bent, the pads of the femur section slide on either side of a central ridge on the tibia section in curved hollowed-out bearing faces of constant width and are forcibly guided by a transverse pin associated with the femur section which passes through a curved slot in the central ridge as set forth in German Offenlegungsschrift No. 2,244,064. As result it is not possible to simulate the natural action of and the physiological conditions prevailing in a healthy knee-joint.

An object of the invention is to make it possible, when the joint is in bent positions, for the femur section to perform a limited, self-adjusting forward movement in relation to the tibia section to suit the attachment of the tendons of the leg and for the prosthesis to permit the lower leg a limited rotary movement relative to the thigh, and also for any screwed assembly of the two parts of the joint to be avoided when an operation is performed to fit the prosthesis.

SUMMARY OF THE INVENTION

In a knee-joint endoprosthesis of the kind hereinabove described, this object is achieved in accordance with the invention by providing the saddle shaped ridge with a fixed guiding cross-shaft which forms a free spigot on either side of the ridge and which lies off and to the rear of the centre axis of the lower shank when the joint is in the extended portion, by making the two curved, hollowed-out bearing faces, and the supporting pads, which conform to the bearing faces in the extended position, diminish in width from front to rear as a result of the ridge becoming wider in the rearwards direction, by having the spigots engage with clearance in guide grooves in the supporting pads which extend approximately parallel to the lower faces of the pads and which open upwards at their rear ends, and by restricting the extension of the two sections of the joint by means of an abutment.

By this means it is possible to produce the femur section and the tibia as finished parts each of which is one unit, to hook the femur section onto the spigots of the tibia section through the open upper ends of the guide grooves of the femur section, and thus to avoid all assembly work involving screwed connections. The fact that the saddle ridge becomes wider towards the rear and conversely that the bearing faces and the supporting pads diminish in width towards the rear means that in any bent position a limited rotary movement is possible for the tibia section relative to the femur section such as exists in a healthy knee joint, and as a result of the additional play which the spigots have in the guide grooves the femur section can, as dictated by the attachment of the leg tendons, which is different in every patient, move forward in relation to the tibia section with a limited movement which is adjusted to the attachment of the leg tendons, which movement is similarly possible for a healthy natural knee joint. The physiological action of the parts of the prosthesis which can be achieved in this way avoids straining the knee's muscular extensor apparatus, in contrast to constructions where there is no mobility on the shaft. Finally the extension of the joint is restricted by an abutment without the parts becoming wedged, in which case it is advantageous for there to be approximately 5° of over-extension in the extended position.

During no movement there are not any pressure loads on the spigots and their function is merely that of guides. In addition, by virtue of a novel manner which has yet to be described of anchoring the parts of the joint in the shin-bone and thigh-bone it is ensured that there is support over a wide area in the shin-bone and thigh-bone.

BRIEF DESCRIPTION OF THE DRAWINGS

In order that the invention may be more clearly understood, reference will now be made to the accompanying drawings, which show one embodiment of a knee-joint endoprosthesis by way of example, and in which:

FIG. 1 is a front view of the knee-joint endoprosthesis and its anchoring shanks in the extended position, FIG. 2 is a rear view of the prosthesis without the anchoring shanks, FIG. 3 is a side-view of the prosthesis, FIG. 4 is a plan view from the upper side of the prosthesis, FIG. 5 is a section through the joint in the direction of the axis of the shank for anchorage in the tibia, FIG. 6 is a section on line VI—VI of FIG. 5, FIG. 7 is a side-view of the tibia section, and FIG. 8 is a plan view related to FIG. 7.

DETAILED DESCRIPTION OF PREFERRED EMBODIMENT

Referring now to the drawings, the knee-joint endoprosthesis shown consists of a lower, tibia section 1 and an upper, femur section 2 which are anchored in the shin-bone and the thigh-bone by means of respective anchoring shanks 3 and 4. The shanks 3 and 4 taper in the directions away from the joint and to obtain a wide area of support they are provided with circumferential ribs 3a and 4a one of whose faces lies perpendicular to the axis of the shank. The shanks 3 and 4 either form units with sections 1 and 2 respectively of the joint or advantageously they may be detachably connected to sections 1 and 2, in which case sections 1 and 2 are each provided with an outwardly tapering conical spigot (5 or 6, FIG. 5) onto which the shanks are a suitably tight fit to remain fixed and unable to turn. To enable the shanks to be detached from sections 1 and 2, opposing wedge-shaped grooves 7 are arranged on the upper side of the femur section 2 and similar wedge-shaped grooves are arranged on the underside of the tibia section, into which a wedge-shaped tool can be engaged to release the shanks if for example sections 1 and 2 become worn and have to be replaced, when the anchoring shanks remain in place in the shin-bone and the thigh-bone.

The tibia section 1 is provided with a central saddle-ridge 9 which becomes broader from the front at 8 towards the rear and which has an abutment boss 10 on the top at the front and whose rear half is of greater height. Where this raised part is situated is mounted a cross-shaft which is situated off the axis of the shank and which advantageously continues on either side into projecting tapering spigots 11. On either side of the saddle, the tibia section 1 is provided with bearing faces 12 which are hollowed out in cross-section and which curve up into a rising part at the front and which diminish in width from front to rear following the outline of the saddle 9. The bearing surfaces are adapted to match the anatomically shaped pads 13 to enable the function of a healthy knee-joint to be simulated physiologically.

The upper, femur section 2 consists of two pads 13 whose lower faces slide on the bearing faces and also revolve past them to some extent, the pads also diminishing in width from front to rear similarly to the bearing faces. At the front end, at 14, the pads are yoked together and this yoke 14 rests against the boss 10 at the front and top of the saddle 9 when the joint is in the extended position. The rear ends 13a of the pads 13 extend upwards past the upper side of the pads.

On the inside faces adjacent the saddle ridge 9, the outline of which faces is matched to the outline of the side-faces of the saddle, both of the pads 13 are provided with a guide groove 15 which lies approximately parallel to the bottom face of the pad and whose width is greater than the diameter of the guide spigots 11 and which advantageously tapers in cross-section in the direction of the bottom of the groove. With the joint in bent positions, the joint spigots 11 have a slight play in the grooves and only in the extended position do the spigots 11 press against the lower sidewalls of the grooves 15. Both grooves 15 are open at their upper, rear ends at 15a so that the open ends 15a of the grooves can be used to hook the femur section 2 onto the spigots 11 with the joint in the bent position and the femur section can be moved to the extended position, when the spigots 11 can slide freely in the grooves 15 until the extended position is reached.

Because of the saddle ridge 9 which becomes broader from front to rear and because of the bearing faces 12 on the tibia section 1 and the pads 13 on the femur section 2 which conversely diminish in width, it is ensured that the position of sections 1 and 2 relative to one another are fixed only in the extended position, whereas at the beginning of a bending movement the front part of the femur section first moves slightly forward relative to the tibia section, as is also the case with a healthy knee-joint, but when it does so the femur section has the capability of moving freely backwards or forwards, by 7 mm for example, due to the play between the spigots 11 and the guide grooves 15, which allows the femur section to adjust to the attachments of the tendons of the leg as it move forwards and thus prevents strain on the knee's muscular extensor apparatus. The play between the spigots 11 and the guide 15, also gives a small amount of additional freedom in bent positions. As a result of the backwardly widening saddle ridge 9 and the bearing faces 12 and pads 13 whose width diminishes in the rearwards direction, a limited turning movement between sections 1 and 2 or of the lower leg relative to the thigh is also possible in all bent positions as in the natural knee-joint.

To keep frictional wear in the prosthesis between the bearing faces and the pads as low as possible the tibia section 1 and the femur section 2 are made from an aluminium oxide (sintered alumina). This material is particularly hard and is noted for its histo compatibility. The two sections 1 and 2 of the joint are connected to the ribbed steel pins 3 and 4 either permanently or else detachably by the clamping action of a taper as already mentioned.

We claim:

1. In a knee-joint endoprosthesis, consisting of a lower tibia section to be anchored in the shin-bone by a lower shank, which section has, on either side of a central ridge which extends from front to rear, a bearing face which rises in a curve towards the front and which is hollowed-out in cross-section, and of a femur section which is to be anchored in the thigh-bone by an upper shank and which is provided with two pads which are yoked together across the ridge and are supported on the bearing faces, the improvement which consists in that a saddle-shaped ridge is provided with a fixed guiding cross-shaft which forms a free spigot on either side of said ridge and which lies off and to the rear of the centre axis of said lower shank when the joint is in the extended position, in that said two curved, hollowed-out bearing faces, and said supporting pads, which conform to said bearing faces in the extended position, diminish in width from front to rear as a result of said ridge becoming wider in the rearward direction, in that said spigots engage with clearance in guide grooves in said supporting pads which extend approximately parallel to the lower faces of said pads and which open upwards at their rear ends, and in that the extension of the two sections of the joint is restricted by an abutment.

2. An endoprosthesis according to claim 1, wherein said bearing faces and said pads have a small clearance between them when the joint is in bent position, and the diameter of said spigots is less than the width of said guide grooves.

3. An endoprosthesis according to claim 1, wherein said spigots taper in the direction of their ends and the width of said guide grooves diminishes in the direction of their lower ends.

4. An endoprosthesis according to claim 1, wherein when the joint is in the extended position said yoke between the front of said pads rests against a boss at the front and top of said saddle ridge and said spigots rest against the lower side-walls of said grooves.

5. An endoprosthesis according to claim 1 wherein said tibia section is provided with a downwardly extending conical spigot and said femur section is provided witn an upwardly directed conical spigot which is set forward, onto which spigots tapering shanks can be inserted so as not to turn, said shanks being provided with circumferential ribs whose supporting faces lie perpendicularly to the axis of the shank.

6. An endoprosthesis according to claim 1 wherein said tibia and femur sections are made from an aluminium oxide (sintered alumina).

* * * * *